United States Patent [19]

Hutchison

[11] Patent Number: 4,968,697
[45] Date of Patent: Nov. 6, 1990

[54] 2-SUBSTITUTED ADENOSINE 5'-CARBOXAMIDES AS ANTIHYPERTENSIVE AGENTS

[75] Inventor: Alan J. Hutchison, Madison, Conn.

[73] Assignee: Ciba-Geigy Corporation, Ardsley, N.Y.

[21] Appl. No.: 389,663

[22] Filed: Aug. 4, 1989

Related U.S. Application Data

[63] Continuation-in-part of Ser. No. 193,967, May 13, 1988, abandoned, which is a continuation-in-part of Ser. No. 150,696, Feb. 1, 1988, abandoned, which is a continuation-in-part of Ser. No. 11,169, Feb. 4, 1987, abandoned.

[51] Int. Cl.$^5$ .................... A61K 31/70; C07H 19/167
[52] U.S. Cl. ........................ 514/46; 514/45; 536/23; 536/24; 536/26
[58] Field of Search ............ 514/45, 46; 536/23, 536/24, 26

[56] References Cited

U.S. PATENT DOCUMENTS

| | | | |
|---|---|---|---|
| 3,212,954 | 10/1965 | Kuhn et al. | 536/26 |
| 3,575,959 | 4/1971 | Shen et al. | 536/26 |
| 3,590,029 | 6/1971 | Koch et al. | 536/26 |
| 3,752,805 | 7/1973 | Maguire et al. | 536/26 |
| 3,838,147 | 9/1974 | Pohlke et al. | 536/26 |
| 3,864,483 | 2/1975 | Stein et al. | 424/180 |
| 3,903,073 | 9/1975 | Prasad et al. | 536/26 |
| 3,936,439 | 2/1976 | Marumoto et al. | 536/26 |
| 3,968,102 | 7/1976 | Suehiro et al. | 536/26 |
| 3,992,531 | 11/1976 | Prasad et al. | 424/180 |
| 4,029,884 | 6/1977 | Stein et al. | 536/26 |
| 4,104,462 | 8/1978 | Fischer et al. | 536/26 |
| 4,167,565 | 9/1979 | Stein et al. | 424/180 |

(List continued on next page.)

FOREIGN PATENT DOCUMENTS

| | | | |
|---|---|---|---|
| 191025 | of 1986 | European Pat. Off. | |
| 0152944 | 8/1986 | European Pat. Off. | 536/26 |
| 0232813 | 8/1987 | European Pat. Off. | 514/46 |
| 0277917 | 8/1988 | European Pat. Off. | 514/46 |
| 2402804 | 7/1975 | Fed. Rep. of Germany | 514/46 |
| 50-101383 | of 1975 | Japan | |
| 8504882 | 11/1985 | PCT Int'l Appl. | 536/26 |
| 8600310 | of 1986 | PCT Int'l Appl. | |
| 2077725 | 12/1981 | United Kingdom | 514/46 |
| 2203149 | of 1988 | United Kingdom | |

OTHER PUBLICATIONS

Prasad et al., J. Med. Chem. 1980, 23, 313–319.
Chem. Abstract, vol. 105 (1986) 126814y.

(List continued on next page.)

*Primary Examiner*—John W. Rollins
*Assistant Examiner*—L. Eric Crane
*Attorney, Agent, or Firm*—Norbert Gruenfeld

[57] ABSTRACT

The compounds of the formula I

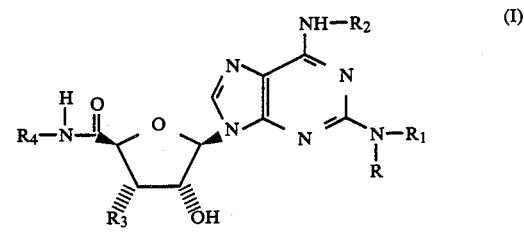

wherein R represents hydrogen or lower alkyl; $R_1$ represents $C_3$–$C_6$-cycloalkyl optionally substituted by lower alkyl, $C_3$–$C_6$-cycloalkyl-lower alkyl optionally substituted by lower alkyl, bicycloalkyl, bicycloalkyl-lower alkyl, aryl, aryl-lower alkyl, aryl-$C_3$–$C_6$-cycloalkyl, 9-fluorenyl, diaryl-lower alkyl, 9-fluorenyl-lower alkyl, cycloalkenyl-lower alkyl, bicycloalkenyl-lower alkyl, tetrahydropyranyl-lower alkyl, tetrahydrothiopyranyl-lower alkyl or adamantyl-lower alkyl; or $R_1$ represents a bicyclic benzo-fused 5- or 6-membered saturated carbocyclic radical or a benzo-fused 5- or 6-membered saturated heterocyclic radical containing a heteroatom selected from oxygen and sulfur which is directly attached to the fused benzene ring, any said bicyclic radical being unsubstituted or substituted on the benzo portion by lower alkyl, lower alkoxy, hydroxy, halogen or trifluoromethyl, or by a substituent -W-Z in which W represents a direct bond, lower alkylene, lower alkenylene, thio-lower alkylene or oxy-lower alkylene and Z represents cyano, carboxy or carboxy derivatized in the form of a pharmaceutically acceptable ester or amide, or $R_1$ represents any said bicyclic radical substituted-lower alkyl; or $R_1$ represents aryl-hydroxy-lower alkyl; $R_2$ represents hydrogen, lower alkyl or aryl-lower alkyl; $R_3$ represents hydrogen or hydroxy; $R_4$ represents hydrogen, lower alkyl, aryl-lower alkyl, $C_3$–$C_6$-cycloalkyl or hydroxy-lower alkyl; aryl represents an optionally substituted carbocyclic aromatic radical, being preferably 1- or 2-naphthyl, phenyl, or naphthyl or phenyl substituted by one to three of lower alkyl, lower alkoxy, hydroxy, halogen or trifluoromethyl, or naphthyl or phenyl substituted by a substitutent -W-Z in which W represents a direct bond, lower alkylene, lower alkenylene, thio-lower alkylene or oxy-lower alkylene and Z represents cyano, carboxy or carboxy derivatized in the form of a pharmaceutically acceptable ester or amide; or aryl represents a heterocyclic aromatic radical, being preferably pyridyl or thienyl, each optionally substituted as described above for phenyl; pharmaceutically acceptable ester derivatives thereof in which free hydroxy groups are esterified in the form of a pharmaceutically acceptable ester; and pharmaceutically acceptable salts thereof; their preparation; and their use as adenosine-2 receptor agonists are disclosed.

15 Claims, No Drawings

U.S. PATENT DOCUMENTS

| | | | |
|---|---|---|---|
| 4,255,565 | 3/1981 | Marumoto et al. | 536/24 |
| 4,258,033 | 3/1981 | Marumoto et al. | 424/180 |
| 4,293,690 | 10/1981 | Sawa et al. | 536/24 |
| 4,341,769 | 6/1982 | Marumoto et al. | 424/180 |
| 4,501,735 | 2/1985 | Trivedi et al. | 514/46 |
| 4,593,019 | 6/1986 | Bristol et al. | 514/46 |
| 4,594,350 | 6/1986 | Vince | 514/261 |
| 4,600,707 | 7/1986 | Patt | 514/46 |
| 4,657,897 | 4/1987 | Bristol et al. | 514/47 |
| 4,657,898 | 4/1987 | Bristol et al. | 514/47 |
| 4,683,223 | 7/1987 | Trivedi | 514/46 |
| 4,714,697 | 8/1987 | Trivedi | 514/46 |
| 4,738,954 | 4/1988 | Hamilton et al. | 514/46 |

OTHER PUBLICATIONS

Madhavan et al., J. Org. Chem., 51, 1287–1293 (1986).
Herdewijin et al., J. Med. Chem. 28, 1385–1386 (1985).
Shealy et al., J. Med. Chem., 27, 670–674 (1984).
Cermak et al., Tetrahedron Letters, 27, 2331–2332 (1981).
Vince et al., J. Org. Chem., 45, 531–533 (1980).
Paulsen et al., Chem. Ber., 114, 346–359 (1981).
Marumoto et al., Chem. Pharm. Bull, 24, 2624–2628 (1976).
Dunham et al., J. Pharm. Exper. Therapeutics, 238, 954–959 (1986).
Marumoto et al., Chem. Pharm. Bull., 32, 759–774 (1975).
Moos et al., J. Med. Chem., 28, 1383–1384 (1985).
Daly et al., Biochemical Pharmacology, 35, 2467–2481 (1986).
Kikugawa et al., "2-substituted-thioadenosines", Chem. Abstr. 84: 31369r (1976).
Asahi Chem. Ind., Chemical Abstracts, 94: 140119m (1981).
Kikugawa et al., Chemical Abstracts, 84: 74578A (1976).
Suehiro et al., Chemical Abstracts, 85: 177889c (1976).
Marumoto et al., J. Takeda Res. Lab., 44, 220–230 (1985).
Hamilton et al., Life Sciences, 41, 2295–2302 (1987).
Omura et al., Chem. Pharm Bull., 29, 1870–1875 (1981).
Montgomery et al., Symposium on Biological Methylation in Drug Research, 1985, R. T. Borchardt ed., Humana, Clifton, N.J., published 1986, 409–416.

2-SUBSTITUTED ADENOSINE 5'-CARBOXAMIDES AS ANTIHYPERTENSIVE AGENTS

CROSS REFERENCE TO RELATED APPLICATIONS

This is a continuation-in-part of application Ser. No. 193,967 filed May 13, 1988 now abandoned which is a continuation in part of application Ser. No. 150,696 filed Feb. 1, 1988 (abandoned), which is a continuation-in-part of application Ser. No. 011,169 filed Feb. 4, 1987 (abandoned).

SUMMARY OF THE INVENTION

The instant invention is directed to certain 2-substituted adenosine-5'-carboxamide derivatives as adenosine receptor ligands, to pharmaceutical compositions thereof, to methods for their preparation, and to their use in mammals as therapeutically effective adenosine receptor agonists.

The compounds of the invention are effective as adenosine, particularly adenosine-2 (A-2) receptor ligands which are useful in mammals as adenosine receptor agonists, particularly as adenosine-2 (A-2) receptor agonists.

Said advantageous properties render the compounds of the invention useful for the treatment of conditions in mammals responsive to selective adenosine receptor stimulation (adenosine agonist activity), particularly to adenosine-2 receptor stimulation (adenosine-2 agonist activity), e.g. cardiovascular conditions such as hypertension, thrombosis and atherosclerosis, also central nervous system conditions comprising psychotic conditions such as schizophrenia, and convulsive disorders such as epilepsy.

DETAILED DESCRIPTION OF THE INVENTION

More specifically, the instant invention is directed to the compounds of the formula I

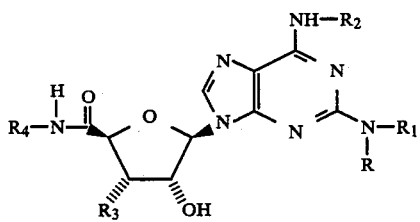

wherein R represents hydrogen or lower alkyl; $R_1$ represents $C_3$–$C_6$-cycloalkyl optionally substituted by lower alkyl, $C_3$–$C_6$-cycloalkyl-lower alkyl optionally substituted by lower alkyl, bicycloalkyl, bicycloalkyl-lower alkyl, aryl, aryl-lower alkyl, aryl-$C_3$–$C_6$-cycloalkyl, 9-fluorenyl, diaryl-lower alkyl, 9-fluorenyl-lower alkyl, cycloalkenyl-lower alkyl, bicycloalkenyl-lower alkyl, tetrahydropyranyl-lower alkyl, tetrahydrothiopyranyl-lower alkyl or adamantyl-lower alkyl: or $R_1$ represents a bicyclic benzo-fused 5- or 6-membered saturated carbocyclic radical or a benzo-fused 5- or 6-membered saturated heterocyclic radical containing a heteroatom selected from oxygen and sulfur which is directly attached to the fused benzene ring, any said bicyclic radical being unsubstituted or substituted on the benzo portion by lower alkyl, lower alkoxy, hydroxy, halogen or trifluoromethyl, or by a substituent -W-Z in which W represents a direct bond, lower alkylene, lower alkenylene, thio-lower alkylene or oxy-lower alkylene and Z represents cyano, carboxy or carboxy derivatized in the form of a pharmaceutically acceptable ester or amide, or $R_1$ represents any said bicyclic radical substituted-lower alkyl; or $R_1$ represents aryl-hydroxy lower alkyl; $R_2$ represents hydrogen, lower alkyl or aryl-lower alkyl; $R_3$ represents hydrogen or hydroxy; $R_4$ represents hydrogen, lower alkyl, aryl-lower alkyl, $C_3$–$C_6$-cycloalkyl or hydroxy-lower alkyl; aryl represents an optionally substituted carbocyclic aromatic radical, being preferably 1- or 2-naphthyl, phenyl, or naphthyl or phenyl substituted by one to three of lower alkyl, lower alkoxy, hydroxy, halogen or trifluoromethyl, or naphthyl or phenyl substituted by a substituent -W-Z in which W represents a direct bond, lower alkylene, lower alkenylene, thio-lower alkylene or oxy-lower alkylene and Z represents cyano, carboxy or carboxy derivatized in the form of a pharmaceutically acceptable ester or amide; or aryl represents a heterocyclic aromatic radical, being preferably pyridyl or thienyl, each optionally substituted as described above for phenyl; pharmaceutically acceptable ester derivatives thereof in which free hydroxy groups are esterified in the form of a pharmaceutically acceptable ester; and pharmaceutically acceptable salts thereof.

Preferred are the compounds of formula I wherein R represents hydrogen or lower alkyl; $R_1$ represents $C_3$–$C_6$-cycloalkyl-lower alkyl; or $R_1$ represents aryl-lower alkyl wherein aryl represents pyridyl, thienyl, naphthyl, phenyl, phenyl substituted by one or two substituents selected from halogen, trifluoromethyl, lower alkoxy, hydroxy and lower alkyl, or phenyl substituted by a substituent -W-Z in which W represents a direct bond, lower alkylene, lower alkenylene, thio-lower alkylene or oxy-lower alkylene, and Z represents cyano, carboxy, carboxy derivatized in the form of a pharmaceutically acceptable ester or carboxy derivatized in the form of a pharmaceutically acceptable amide; or $R_1$ represents a substituent of the formula B

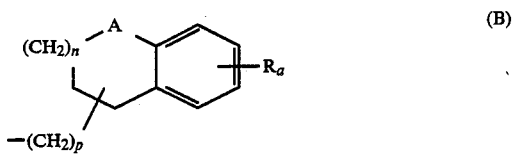

in which A represents methylene, oxy or thio, n represents zero or one, p represents zero, one or two, and $R_a$ represents hydrogen, lower alkyl, lower alkoxy, halogen or -W-Z as defined above; $R_2$ represents hydrogen or lower alkyl; $R_3$ represents hydrogen or hydroxy; $R_4$ represents hydrogen, lower alkyl, $C_3$–$C_6$-cycloalkyl, hydroxy-lower alkyl, or aryl-lower alkyl in which aryl represents pyridyl, thienyl or phenyl; pharmaceutically acceptable ester derivatives thereof in which one or more free hydroxy groups are esterified in the form of a pharmaceutically acceptable ester; and pharmaceutically acceptable salts thereof.

Preferred are the compounds of formula (Ia)

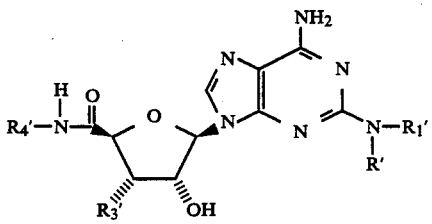

wherein R' represents hydrogen or lower alkyl; R₁' represents C₃–C₆-cycloalkyl-lower alkyl; or R₁' represents aryl-lower alkyl in which aryl represents thienyl, pyridyl, phenyl or phenyl monosubstituted by halogen, trifluoromethyl, lower alkoxy, hydroxy, lower alkyl, or by a substituent -W-Z in which W represents a direct bond, lower alkylene, thio-lower alkylene or oxy-lower alkylene, and Z represents cyano, carboxy, lower alkoxycarbonyl, carbamoyl, N-mono- or N,N-di-lower alkylcarbamoyl; or Rl' represents a substituent of the formula B'

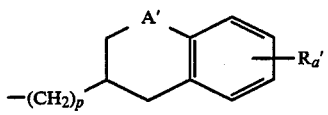

in which A' represents a direct bond, methylene, oxy or thio, p represents zero, one or two and $R_a'$ represents hydrogen, lower alkyl, lower alkoxy, hydroxy, halogen or -W-Z as defined above; or R₁' represents aryl-hydroxy-lower alkyl in which aryl has meaning as defined above; R₃' represents hydrogen or hydroxy; and R₄' represents hydrogen, lower alkyl, C₃–C₆-cycloalkyl or hydroxy-lower alkyl; pharmaceutically acceptable prodrug ester derivatives thereof in which one or more free hydroxy groups are esterified in the form of a pharmaceutically acceptable ester; and pharmaceutically acceptable salts thereof.

Preferred are the said compounds of formula I and Ia wherein R₃ and R₃', respectively, represent hydroxy, and ester derivatives thereof.

Particularly preferred are the compounds of formula Ia above wherein R₃' represents hydroxy; R₄' represents lower alkyl, cyclopropyl or hydroxy-lower alkyl; and R', R₁', A', p and $R_a'$ have meaning as defined above; pharmaceutically acceptable prodrug ester derivatives thereof in which free hydroxy groups are esterified in the form of a pharmaceutically acceptable ester; and pharmaceutically acceptable salts thereof.

Further preferred are the compounds of formula II

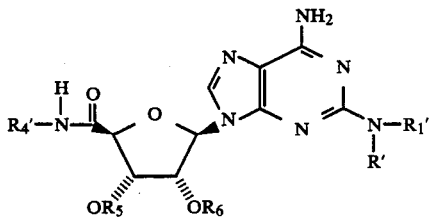

wherein R' represents hydrogen or C₁–C₄-alkyl; R₁' represents (C₅- or C₆)-cycloalkyl-C₁–C₄-alkyl, or R₁' represents aryl-C₁–C₄-alkyl in which aryl represents 2- or 3-thienyl, 2-, 3- or 4-pyridyl, phenyl, or phenyl monosubstituted by halogen, trifluoromethyl, lower alkoxy, lower alkyl or by a substituent -W-Z in which W represents a direct bond, C₁–C₄-alkylene, thio-C₁–C₃-alkylene or oxy-C₁–C₃-alkylene and Z represents cyano, carboxy, lower alkoxycarbonyl, carbamoyl, N-mono- or N,N-di-lower alkylcarbamoyl; or R₁' represents aryl-hydroxy-C₁–C₄-alkyl in which aryl has meaning as defined above; R₄' represents C₁–C₄-alkyl, cyclopropyl or hydroxy-C₂–C₄-alkyl; R₅ and R₆ represent hydrogen, lower alkanoyl, lower alkoxy-lower alkanoyl, aroyl, carbamoyl, mono- or di-lower alkylcarbamoyl; and pharmaceutically acceptable salts thereof.

Particular preferred are said compounds of formula II wherein R' represents C₁–C₃-alkyl or hydrogen; R₁' represents CH₂CH₂-(cyclohexyl or cyclopentyl); or R₁' represents -CH₂CH₂-aryl in which aryl represents 2- or 3-pyridyl, phenyl, or phenyl monosubstituted by a substituent -CH₂CH₂-Z or -OCH₂-Z in which Z represents cyano, carboxy, lower alkoxycarbonyl, carbamoyl, N-mono- or N,N-di-lower alkylcarbamoyl; R₄' represents ethyl or hydroxyethyl; R₅ and R₆ represent hydrogen, lower alkanoyl or lower alkoxy-C₂–C₄-alkanoyl; and pharmaceutically acceptable salts thereof.

Most preferred are the compounds of formula II wherein R' represents hydrogen or methyl; R₁' represents cyclohexylethyl; or R₁' represents 2-phenylethyl, 2-(2-pyridyl)-ethyl or 2-phenylethyl substituted in the para position by CH₂CH₂Z in which Z represents carboxy, lower alkoxycarbonyl, carbamoyl or mono-lower alkylcarbamoyl: R₄' represents ethyl: R₅ and R₆ represent hydrogen; and pharmaceutically acceptable salts thereof.

A particular preferred embodiment of the invention is also represented by the compounds of formula IIa

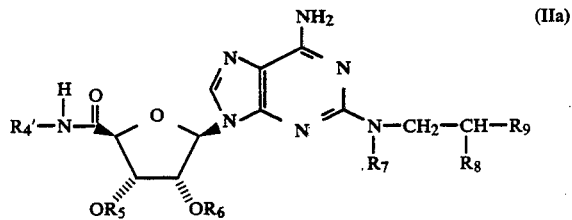

wherein R₄' represents ethyl; R₅ and R₆ represent hydrogen or lower alkanoyl; R₇ represents hydrogen or methyl; R₈ represents hydrogen or methyl; R₉ represents cyclohexyl, phenyl, or phenyl monosubstituted by halogen, trifluoromethyl, lower alkyl, lower alkoxy or -CH₂CH₂-Z in which Z represents carboxy or lower alkoxycarbonyl; and pharmaceutically acceptable salts thereof.

Particular embodiments of the invention relate to the compounds cited hereinabove wherein in formula I R represents hydrogen, in formula Ia R' represents hydrogen, in formula II R' represents hydrogen and in formula IIa R₇ represents hydrogen.

The general definitions used herein have the following meaning within the scope of the present invention.

The term "lower" referred to above and hereinafter in connection with organic radicals or compounds respectively defines such with up to and including 7, preferably up to and including 4 and advantageously one or two carbon atoms.

A lower alkyl group is straight chain or branched and preferably contains 1 to 4 carbon atoms, and represents for example ethyl, propyl, butyl, and advantageously methyl.

A lower alkoxy group is straight chain or branched and preferably contains 1 to 4 carbon atoms, and represents for example methoxy, ethoxy, propoxy.

Lower alkylene is straight chain or branched alkylene and preferably contains 1 to 4 carbon atoms, and represents for example methylene, ethylene.

Lower alkenylene is straight chain or branched alkenylene; preferably contains 2 to 4 carbon atoms and represents for example ethenylene, 1- or 2-propenylene.

Halogen is preferably chloro, but may also be fluoro, bromo or iodo.

Cycloalkyl represents preferably 3 to 6 ring membered cycloalkyl, i.e. $C_3$-$C_6$-cycloalkyl.

$C_3$-$C_6$-cycloalkyl represents cyclopropyl, cyclobutyl, cyclopentyl or cyclohexyl, preferably cyclopropyl.

Cycloalkyl-lower alkyl represents preferably (cyclopentyl or cyclohexyl)-$C_1$-$C_4$-alkyl, advantageously 1- or 2-(cyclopentyl or cyclohexyl)-ethyl, propyl or butyl.

Bicycloalkyl represents preferably bicycloheptyl or bicycloheptyl substituted by lower alkyl, particularly unsubstituted or lower alkyl substituted bicyclo[2,2,1]-heptyl, such as bornyl, neobornyl, isobornyl, norbornyl, e.g. 2-norbornyl. The term bornyl is synonymous with bornanyl.

Cycloalkenyl-lower alkyl represents preferably 1-cyclohexenyl-lower alkyl.

Tetrahydropyranyl represents preferably 4-tetrahydropyranyl.

Tetrahydrothiopyranyl represents preferably 4-tetrahydrothiopyranyl.

Bicycloalkenyl represents preferably bicycloheptenyl or bicycloheptenyl substituted by lower alkyl, particularly unsubstituted or lower alkyl-substituted bicyclo[2.2.1]heptenyl, such as 5-norbornen-2-yl, or unsubstituted or lower alkyl-substituted bicyclo[3.1.1]heptenyl, such as 6,6-dimethylbicyclo[3.1.1]hept-2-en-2-yl.

Adamantyl represents preferably 1-adamantyl.

Aryl is an optionally substituted carbocyclic or heterocyclic aromatic radical, a carbocyclic aromatic radical being preferably phenyl or 1- or 2-naphthyl each optionally substituted by one to three of lower alkyl, lower alkoxy, hydroxy, halogen or trifluoromethyl, or by a substituent -W-Z in which W represents a direct bond, lower alkylene, thio-lower alkylene or oxy-lower alkylene and Z represents cyano, carboxy or carboxy derivatized in the form of a pharmaceutically acceptable ester or amide; and a heterocyclic aromatic radical being preferably pyridyl or thienyl. Advantageously aryl represents phenyl or phenyl substituted as described above.

Aryl-lower alkyl represents preferably aryl-$C_1$-$C_4$-alkyl in which aryl represents a carbocyclic or heterocyclic aromatic radical as defined above, e.g. benzyl or 1- or 2-phenyl-(ethyl, propyl or butyl), each unsubstituted or substituted on phenyl ring as defined under aryl above; or 2-, 3- or 4-pyridylmethyl or 2-(2-, 3- or 4-pyridyl)-(ethyl, propyl or butyl); or 1- or 2-naphthylmethyl or 2-(1- or 2-naphthyl)-(ethyl, propyl or butyl).

Aryl-hydroxy-lower alkyl represents preferably aryl-hydroxy-$C_1$-$C_4$-alkyl in which aryl preferably represents a carbocyclic aromatic radical as defined above, e.g. 2-phenyl-2-hydroxy-(ethyl, propyl or butyl).

Diaryl-lower alkyl represents preferably diphenyl-$C_1$-$C_4$-alkyl, e.g. omega-diphenyl- (methyl, ethyl or propyl).

Hydroxy-lower alkyl represents preferably 2-, 3- or 4-hydroxy-$C_2$-$C_4$-alkyl, advantageously hydroxyethyl.

Pyridyl represents 2-, 3- or 4-pyridyl, advantageously 2- or 3-pyridyl.

Thienyl represents 2- or 3-thienyl.

Aryl-cycloalkyl represents preferably phenyl-$C_3$-$C_6$-cycloalkyl, for example 2-phenylcyclohexyl or 2-phenylcyclopropyl.

A bicyclic benzo-fused 5- or 6-membered saturated carbocyclic radical, as a substituent $R_1$ depicted by formula B above in which A represents methylene, represents preferably 1,2,3,4-tetrahydro-2-naphthyl or 2-indanyl, each unsubstituted or substituted on benzo portion as indicated above for phenyl under aryl.

A bicyclic benzo-fused 5- or 6-membered saturated heterocyclic radical, as a substituent depicted by formula B above in which A represents oxy or thio, represents preferably 3,4-dihydro-2H-[1]-3-benzopyranyl or 3,4-dihydro-2H-[1]-3-benzothiopyranyl, each unsubstituted or substituted on the benzo portion as indicated above for phenyl under aryl.

A lower alkoxycarbonyl group preferably contains 1–4 carbon atoms in the alkoxy portion and represents for example: methoxycarbonyl, propoxycarbonyl, isopropoxycarbonyl or advantageously ethoxycarbonyl.

Lower alkanoyl represents preferably straight chain or branched $C_1$-$C_4$-alkanoyl, e.g. acetyl, isobutyryl, pivaloyl.

Lower alkoxy-lower alkanoyl represents preferably lower alkoxy-$C_2$-$C_4$-alkanoyl, e.g. methoxyacetyl, 3-ethoxypropionyl.

Aroyl represents preferably benzoyl, benzoyl substituted by one to three of lower alkyl, lower alkoxy, halogen or trifluoromethyl; 2-, 3- or 4-pyridylcarbonyl; or 2- or 3-thienylcarbonyl.

Mono- and di-lower alkylcarbamoyl represents for example N-methyl-, N-ethyl-, N,N-dimethyl- and N,N-diethylcarbamoyl.

Carboxy esterified in the form of a pharmaceutically acceptable ester represents advantageously an ester that may be convertible by solvolysis or under physiological conditions to the free carboxylic acid, e.g. lower alkoxycarbonyl; (amino, mono- or di-lower alkylamino)-substituted lower alkoxycarbonyl; carboxy substituted lower alkoxycarbonyl, e.g. alpha-carboxy-substituted lower alkoxycarbonyl; lower alkoxycarbonyl-substituted lower alkoxycarbonyl, e.g. alpha-lower alkoxycarbonyl-substituted lower alkoxycarbonyl; aryl-substituted lower alkoxycarbonyl, e.g. optionally substituted benzyloxy carbonyl or pyridylmethoxycarbonyl; (hydroxy, lower alkanoyloxy or lower alkoxy)-substituted lower alkoxycarbonyl, e.g. pivaloyloxymethoxycarbonyl; (hydroxy, lower alkanoyloxy or lower alkoxy)-substituted lower alkoxymethoxycarbonyl; bicycloalkoxycarbonyl-substituted lower alkoxycarbonyl, e.g. bicyclo[2,2,1]-heptyloxycarbonyl-substituted lower alkoxycarbonyl, especially bicyclo[2,2,1]heptyloxycarbonyl-substituted methoxycarbonyl such as bornyloxycarbonylmethoxycarbonyl; 3-phthalidoxycarbonyl; (lower alkyl, lower alkoxy, halo)-substituted 3-phthalidoxycarbonyl; lower alkoxycarbonyloxy-lower alkoxycarbonyl, e.g. 1-(methoxy- or ethoxycarbonyloxy)-ethoxycarbonyl; aryloxycarbonyl, e.g. phenoxycarbonyl or phenoxycarbonyl advantageously substituted at the ortho position by carboxy or lower alkoxycarbonyl. Preferred are the lower alkyl esters, omega-(di-lower alkylamino)-alkyl esters, e.g. the di-($C_1$-$C_4$-alkylamino)-ethyl esters, and pivaloyloxymethyl esters.

Carboxy derivatized in the form of a pharmaceutically acceptable amide represents preferably carbamoyl, mono-lower alkylcarbamoyl or di-lower alkylcarbamoyl.

Carboxy derivatized in form of a pharmaceutically acceptable amide futher represents $C_1$-$C_{20}$-alkylcarbamoyl, di-$C_1$-$C_{20}$-alkyl-carbamoyl, aryl-lower alkylcarbamoyl, di-lower alkylamino-lower alkylcarbamoyl, (pyrrolidino, piperidino or morpholino)-lower alkylcarbamoyl, 2-oxopyrrolidino-lower alkylcarbamoyl, morpholinocarbonyl, piperidinocarbonyl unsubstituted or substituted with aryl-lower alkyl, aryl, or lower alkylcarbonyl, or piperazinocarbonyl substituted at the 4-position with aryl-lower alkyl, aryl or lower alkylcarbonyl. Aryl in the above represents preferably phenyl, phenyl substituted by lower alkyl, lower alkoxy, hydroxy, halogen or trifluoromethyl, or heteroaryl such as indolyl (advantageously 3-indolyl) or pyridyl.

The pharmaceutically acceptable ester derivatives in which one or more free hydroxy groups are esterified in the form of a pharmaceutically acceptable ester are particularly prodrug esters that may be convertible by solvolysis under physiological conditions to the compounds of formula I having free hydroxy groups.

Preferred as said prodrug pharmaceutically acceptable esters are straight chain or branched lower alkanoic acid esters, e.g., the acetic, isobutyric, pivaloic acid esters; lower alkoxy-lower alkanoic acid esters, e.g., the methoxyacetic, 3-ethoxypropionic acid esters; arylcarboxylic acid esters, e.g., the benzoic, nicotinic acid esters; carbamic and mono or di-lower alkylcarbamic acid esters (carbamates), e.g. the mono- or di-ethylcarbamic or N-mono- or di-methylcarbamic acid esters. Most preferred are the lower alkanoic acid and lower alkoxyalkanoic acid esters.

Pharmaceutically acceptable salts are generally acid addition salts, which are preferably such of therapeutically acceptable inorganic or organic acids, such as strong mineral acids, for example hydrohalic, e.g. hydrochloric or hydrobromic acid; sulfuric, phosphoric or nitric acid; aliphatic or aromatic carboxylic or sulfonic acids, e.g. formic, acetic, propionic, succinic, glycollic, lactic, malic, tartaric, gluconic, citric, maleic, fumaric, pyruvic, phenylacetic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, benzenesulfonic, p-toluenesulfonic, naphthalenesulfonic, sulfanilic, cyclohexylsulfamic acid; or ascorbic acid. For compounds having a free carboxy group, pharmaceutically acceptable salts are also derived from bases, e.g. alkali metal salts, such as the sodium salt, or salts derived from pharmaceutically acceptable amines, such as tromethamine.

The novel compounds of the invention are active in state of the art in vitro and in vivo test systems, indicative of adenosine receptor agonist activity in mammals.

The adenosine receptor agonists of the invention are useful in mammals including man for the treatment of central nervous system disorders, particularly psychoses such as schizophrenia, and of cardiovascular disorders, particularly hypertension and thrombosis.

The above-cited properties are demonstrable in in vitro and in vivo tests, using advantageously mammals, e.g. rats, dogs, monkeys or isolated organs, tissues and preparations thereof. Said compounds can be applied in vitro in the form of solutions, e.g. preferably aqueous solutions, and in vivo either enterally or parenterally advantageously orally or intravenously, e.g. within gelatin capsules, as starch suspensions or in aqueous solutions. The dosage in vitro may range between about $10^{-5}$ molar and $10^{-9}$ molar concentrations. The dosage in vivo may range between about 0.001 and 25 mg/kg/day, preferably between about 0.0025 and 10 mg/kg/day depending on the compound and the route of administration.

Adenosine-2 (A-2) receptor binding properties, indicative of the adenosine-2 receptor agonist activity of the compounds of the invention are determined in vitro by determining their ability to inhibit the specific binding of 3H-5'-N-ethylcarboxamidoadenosine ($^3$H-NECA), e.g. essentially as described by R. F. Bruns et al, Mol. Pharmacol. 29, 331 (1986), in striatal membrane preparations from corpus striatum of male Sprague-Dawley rats. The concentration of a particular compound required to displace the specific binding of 4 nM $^3$H-NECA is determined in the presence of 50 nM cyclopentyladenosine.

Adenosine-1 (A-1) receptor binding properties of the compounds of the invention indicative of adenosine-1-receptor agonist activity are determined, e.g., essentially according to R. F. Bruns et al in Proc. Natl. Acad. Sci. U.S.A. 77:5547 (1980), by determining their ability to inhibit the specific binding of $^3$H-cyclohexyladenosine ($^3$H-CHA) in rat brain membrane preparations from male Sprague-Dawley rats. The concentration of a particular compound required to displace the specific binding of 1 nM $^3$H-CHA is determined.

Selectivity for the adenosine-2 (A-2) receptor can be ascertained by comparing the relative potency in the two adenosine receptor assays.

Indicative of in vivo adenosine receptor agonist activity, the hypotensive activity of the compounds of the invention as well as their effect on heart rate can be measured in normotensive or spontaneous hypertensive rats on intravenous or oral administration.

Typically, the blood pressure lowering effect in normotensive rats can be determined as follows:

Adult male rats weighing 300–400 g are anesthetized using Inactin (100 mg/kg, i.p.). A femoral artery and contralateral vein are cannulated for direct blood pressure measurement and i.v. drug administration, respectively. Animals are allowed a 15 minute equilibration period before testing. Vehicle (1 ml/kg, i.v.) is administered over a 30 second period followed by a 0.3 ml saline flush administered over a 30 second period. Changes in diastolic blood pressure are recorded using a Beckman polygraph while heart rate is recorded as a derivative of the blood pressure pulse. The test compound is administered in the same manner as vehicle and a dose response curve is established. Percent changes in heart rate and blood pressure are recorded.

The blood pressure lowering effect in the spontaneous hypertensive rat is determined on oral administration.

Antipsychotic activity can be demonstrated e.g. by measuring the inhibition of one-way conditioned avoidance or Sidman avoidance in the rat, or by measuring the antagonism of the behavioral stimulant effects of apomorphine.

Antithrombotic activity can be demonstrated by measuring the inhibition of collagen-induced platelet aggregation.

The compounds of the invention which are selective as adenosine-2 receptor agonists effectively lower blood pressure without any significant decrease in heart rate.

Most selective as adenosine-2 receptor agonists and preferred are the compounds of formula II and IIa as defined above.

Illustrative of the invention, the compounds of Example 1 and example 2g have an IC$_{50}$ of about $2 \times 10^{-8}$M in the in vitro adenosine-2 receptor binding assay, and the compound of example 2 g lowers blood pressure at a dose as low as about 0.005 mg/Kg i.v. in the normotensive rat, or about 3 mg/Kg p.o. on the spontaneous hypertensive rat; further illustrative of the invention, the compound of example 2n has an IC$_{50}$ of about $1.3 \times 10^{-8}$M in the said in vitro assay.

Said compound of example 2 g is about 100 fold more selective for the A-2 than for the A-1 receptor in vitro.

The compounds of the invention, i.e. of formula I and herein cited derivatives thereof, are preferably prepared by process (a) which comprises condensing a compound of the formula

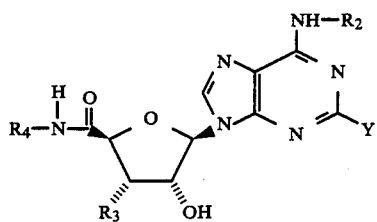

III wherein R$_2$, R$_3$ and R$_4$ have meaning as defined above and Y represents a leaving group, with a compound of the formula

 IV wherein R and R$_1$ have meaning as defined above; and, as required, temporarily protecting any interfering reactive group(s) in the starting materials and then subsequently removing the protecting groups to yield a resulting compound of formula I; and, if desired, converting a resulting compound of formula I into another of the invention, and if desired, converting a resulting free compound into a salt or a resulting salt into a free compound or into another salt, and if required, separating any mixture of isomers or racemates obtained into the single isomers or racemates, and if required, resolving a racemate into the optical antipodes.

The compounds of the invention may also be prepared by process (b) which comprises condensing a compound of the formula

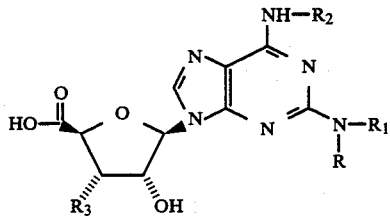

V wherein R$_1$, R$_2$ and R$_3$ have meaning as defined above, or a reactive functional derivative thereof, with an amine of the formula VI

 VI wherein R$_4$ has meaning as defined above; and, as required, temporarily protecting any interfering reactive group(s) in the starting materials and then subsequently removing the protecting groups to yield a resulting compound of formula I; and, if desired, converting a resulting compound of formula I into another of the invention, and if desired, converting a resulting free compound into a salt or a resulting salt into a free compound or into another salt, and if required, separating any mixture of isomers or racemates obtained into the single isomers or racemates, and if required, resolving a racemate into the optical antipodes.

A leaving group in the above processes represents especially halo, for example chloro, bromo or iodo, aliphatically or aromatically substituted sulfonyloxy, for example methylsulfonyloxy or 4-methylphenylsulfonyloxy (tosyloxy), or aliphatically substituted thio, for example lower alkylthio such as methylthio.

In the processes cited herein, reactive functional derivatives of carboxylic acids represent, for example, anhydrides especially mixed anhydrides, acid halides, acid azides, lower alkyl esters and activated esters thereof. Mixed anhydrides are preferably such from pivalic acid, or a lower alkyl (ethyl, isobutyl) hemiester of carbonic acid; acid halides are for example chlorides or bromides; activated esters are for example succinimido, phhthalimido or 4-nitrophenyl esters; lower alkyl esters are for example the methyl or ethyl esters.

In starting compounds and intermediates which are converted to the compounds of the invention in a manner described herein, functional groups present, such as amino and hydroxy, are optionally protected by conventional protecting groups that are common in preparative organic chemistry. Protected amino and hydroxy groups are those that can be converted under mild conditions into free amino and hydroxy groups without the molecular framework being destroyed or undesired side reactions taking place.

Well-known protecting groups that meet these conditions and their introduction and removal are described, for example, in J. F. W. McOmie, "Protective Groups in Organic Chemistry", Plenum Press, London, New York 1973, T. W. Greene, and "Protective Groups in Organic Synthesis", Wiley, New York 1984.

For example, a hydroxy group may be protected in the form of esters, e.g. as acyl derivatives such as the lower alkanoyl, benzoyl, benzyloxycarbonyl or lower alkoxycarbonyl esters, or such hydroxy group may be protected in the form of ethers, e.g. as the lower alkyl,2-tetrahydropyranyl, trityl or benzyl ethers.

Hydroxy groups on adjacent carbon atoms can also be protected e.g. in the form of ketals or acetals, such as lower alkylidene e.g. isopropylidene, benzylidene or 5- or 6-membered cycloalkylidene e.g. cyclopentylidene or cyclohexylidene derivatives.

In a resulting protected compound of formula I or intermediate, in which one or more of the functional groups are protected, the protected functional groups, e.g. hydroxy groups, can be liberated in a manner known per se, e.g. by means of solvolysis, especially hydrolysis with acid, or by hydrogenolysis.

The preparation of the compounds of the invention according to process a) which involves the displacement of a leaving group Y (e.g. chloro) in a compound of the formula III or a protected derivative by an amine of the formula IV is preferably carried out at elevated temperature, e.g. at a temperature ranging from about 75° to 150° C., with an excess of the amine, in the absence or presence of a solvent, particularly a polar solvent such as dimethylformamide, or under elevated pressure, or in the presence of a base such as triethylamine or potassium carbonate.

The starting materials of formula III can be prepared by condensing a compound of the formula VII

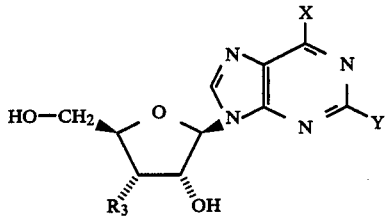

or a compound of formula VII in partially protected form, wherein X and Y represent a leaving group, and $R_3$ has meaning as defined above, with a compound of the formula VIII

$R_2$—$NH_2$  VIII wherein $R_2$ has meaning as defined above; oxidizing the primary alcohol group in a resulting compound of formula IX

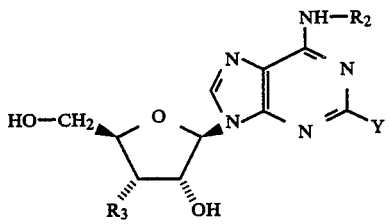

in which any secondary hydroxy groups are in protected form, and wherein Y, $R_2$ and $R_3$ have meaning as defined above, to the corresponding carboxylic acid; and converting said carboxylic acid to a corresponding amide of formula III.

The intermediates of formula VII, and protected derivatives thereof, e.g. in which X and Y represent halogen, particularly chloro, are known or are prepared according to methods known in the art relating to N-(β-D-ribofuranosyl)-purine derivatives, for example as described in Chem. Pharm. Bull. 23, 758 (1975).

The displacement of the leaving group X in a compound of formula VII with an amine of formula VIII is carried out essentially as described above for process (a), preferably using about one mole equivalent of the amine, so as to minimize the displacement of the less reactive leaving group Y.

The oxidation of the resulting e.g. 2-halo substituted adenosine derivatives, in which secondary hydroxy groups are in protected form, is carried out for example with potassium permanganate as described in U.S. Pat. No. 4,167,565.

The resulting carboxylic acid is then first converted to a reactive derivative thereof, e.g. the acid chloride, which is condensed with an amine of the formula VI under condition well-known in the art, e.g. as described in U.S. Pat. No. 4,167,565.

The starting materials of formula IV, VI and VIII are either known in the art, or are prepared using methods known in the art, and as described herein.

The preparation of the compounds of the invention according to process (b) involving the conversion of an acid of formula V to a compound of formula I can be carried out using methodology as described above.

The compounds of the invention or intermediates leading thereto can be converted into other compounds of the invention or corresponding intermediates using chemical methodology known in the art and as illustrated herein.

The conversion of compounds of formula I containing free hydroxy groups to ester derivatives thereof may be carried out by condensation with a corresponding carboxylic acid, advantageously as a reactive functional derivative thereof, according to acylation (esterification) procedures well-known in the art.

A compound of the invention with both 2'- and 3'-hydroxy groups, e.g. a compound of formula I or Ia wherein $R_3$ or $R_3'$ represents hydroxy and wherein both of the adjacent 2'- and 3'-hydroxy groups are protected in the form of ether, acetal or ketal derivatives as described above, e.g. as the isopropylidene (acetonide) derivative, can be converted to a compound of formula I or Ia wherein $R_3$ or $R_3'$ represents hydrogen by elimination of the 3'-substituent by treatment with a strong base, e.g. sodium hydride in anhydrous isopropanol (sodium isopropoxide) to first yield compound with a double bond between the 3'-4'-carbon atoms, said double bond being subsequently reduced, e.g. by catalytic hydrogenation.

The conversion of the compounds of formula I into pharmaceutically acceptable esters, wherein the 2'-hydroxy group (and 3'-hydroxy group if present) is esterified, can be carried out by condensation with a corresponding carboxylic acid or reactive derivative thereof, according to esterification procedures known in the art relating to nucleoside chemistry. For example, an appropriate carboxylic acid anhydride such as acetic anhydride is condensed with a compound of formula I in the presence of asuitable base, e.g. pyridine, triethylamine, 4-(dimethyl-amino)-pyridine, in an inert solvent such as acetonitrile.

A compound of formula I containing a primary amino group (e.g. wherein $NRR_1$ or $NHR_2 = NH_2$) may be converted to a compound of formula I wherein $NRR_1$ or $NHR_2$ represents a secondary amino group, e.g. wherein $R_1$ or $R_2$ represents e.g. aryl-lower alkyl, by treatment with a reactive derivative of the alcohol corresponding to $R_1$ or $R_2$, e.g. with an aryl-lower alkyl halide such as an aryl-lower alkyl iodide, according to methodology well-known in the art for alkylation of amines. Similarly, a secondary amine wherein R represents hydrogen may be converted to a tertiary amine wherein R represents lower alkyl.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures preferably near the boiling point for the solvents used, and at atmospheric or superatmospheric pressure.

The invention further includes any variant of the present processes, in which an intermediate product obtainable at any stage thereof is used as starting material and the remaining steps are carried out, or in which the starting materials are formed under the reaction conditions, or in which the reaction components are used in the form of their salts or optically pure antipodes. Whenever desirable, the above processes are carried out after first suitably protecting any potentially interfering reactive functional groups, as illustrated herein.

Advantageously, those starting materials should be used in said reactions that lead to the formation of those compounds indicated above as being preferred.

The invention also relates to novel starting materials and processes for their manufacture.

Depending on the choice of starting materials and methods, the new compounds may be in the form of isomers, for example, as diastereomers, as optical isomers (antipodes), as racemates, or as mixtures thereof.

In case diastereomeric mixtures of the above compounds or intermediates are obtained, these can be separated into the single racemic or optically active isomers by methods in themselves known, e.g. by fractional distillation, crystallization or chromatography.

Any racemic products of formula I or basic intermediates can be resolved into the optical antipodes, for example, by separation of diastereomeric salts thereof, e.g., by the fractional crystallization of d- or l-(tartrate, dibenzoyltartrate, mandelate or camphorsulfonate) salts.

Advantageously, the more active of the antipodes of the compounds of this invention is isolated.

Finally, the compounds of the invention are either obtained in the free form, or as a salt thereof. For example, any resulting free base can be converted into a corresponding acid addition salt, preferably with the use of a pharmaceutically acceptable acid or anion exchange preparation, or resulting salts can be converted into the corresponding free bases, for example, with the use of a stronger base, such as a metal or ammonium hydroxide, or any basic salt, e.g., an alkali metal hydroxide or carbonate, or a cation exchange preparation. These or other salts, for example, the picrates, can also be used for purification of the bases obtained; the bases are then first converted into salts. In view of the close relationship between the free compounds and the compounds in the form of their salts, whenever a compound is referred to in this context, a corresponding salt is also intended, provided such is possible or appropriate under the circumstances.

The compounds, including their salts, may also be obtained in the form of their hydrates, or include other solvents used for the crystallization.

The present invention also relates to the use of the compounds of the invention for the preparation of pharmaceutical compositions, especially pharmaceutical compositions having selective adenosine-2 receptor stimulating activity which can be used for the treatment of e.g. psychotic conditions, such as schizophrenia, and cardiovascular conditions, such as hypertension, thrombosis and atherosclerosis.

The pharmaceutical compositions according to the invention are those suitable for enteral, such as oral or rectal, transdermal and parenteral administration to mammals, including man, for the treatment of diseases responsive to adenosine-2 receptor stimulation (agonist activity) as given above, such as hypertension, comprising an effective adenosine-2 receptor stimulating amount of a compound of the invention, alone or in combination with one or more pharmaceutically acceptable carriers.

The pharmacologically active compounds of the invention are incorporated into pharmaceutical compositions comprising an effective amount thereof in conjunction or admixture with excipients or carriers suitable for either enteral or parenteral application. Preferred are tablets and gelatin capsules comprising the active ingredient together with (a) diluents, e.g. lactose, dextrose, sucrose, mannitol, sorbitol, cellulose and/or glycine; (b) lubricants, e.g. silica, talcum, stearic acid, its magnesium or calcium salts and/or polyethylene glycol; for tablets also (c) binders, e.g. magnesium aluminum silicate, starch paste, gelatin, tragacanth, methylcellulose, sodium carboxymethylcellulose and/or polyvinylpyrrolidone; if desired, (d) disintegrants, e.g. starches, agar, alginic acid or its sodium salt, or effervescent mixtures; and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

The present invention also relates to the use of compounds of the invention having adenosine-2 receptor stimulating (agonist) properties and pharmaceutical compositions comprising said compounds for the treatment in mammals of disorders responsive to selective adenosine-2 receptor stimulation (agonist activity), particularly psychotic conditions (e.g. schizophenia) and cardiovascular conditions (e.g. hypertension and thrombosis).

One aspect relates advantageously to the method of treatment of cardiovascular disorders in mammals, e.g. such responsive to adenosine-2 receptor stimulation (agonist activity), for example hypertension, using an effective amount of a compound of the invention, preferably in the form of above-cited pharmaceutical compositions.

The dosage of active compound administered is dependent on the species of warm-blooded animal (mammal), the body weight, age and individual condition, and on the form of administration.

A unit dosage for a mammal of about 50 to 70 kg may contain between about 5 and 100 mg of the active ingredient.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. The structure of final products, intermediates and starting materials is confirmed by analytical methods, e.g. microanalysis and spectroscopic characteristics (e.g. MS, IR, NMR).

The numbering of the positions of the adenine or purine ring system is as conventionally used in the art (e.g. Merck Index, tenth edition).

EXAMPLE 1

A mixture of 1.15 g of 2-(2-phenethylamino)-2',3'-O-isopropylidene-adenosine-5'-(N-ethyl)-carboxamide and 25 ml of 1N hydrochloric acid is heated at 65° for 1 hour The reaction mixture is neutralized and the product is extracted with ethyl acetate. After drying over $MgSO_4$, the solvent is removed in vacuo and the residue is triturated with ether to afford 2-(2-phenethylamino)-adenosine-5'-(N-ethyl)-carboxamide, m.p. 115°–118°.

The starting material is prepared as follows:

A mixture of 1.04 g of 2-chloro-2',3'-O-isopropylidene-adenosine-5'-(N-ethyl)-carboxamide (U.S. Pat. No. 4,167,565) and 8 g of 2-phenethylamine is heated at 130° for 2 hours. After cooling the excess 2-phenethylamine is removed in vacuo and the residue is chromatographed on silica gel with 5% methanol in methylene chloride as the eluent to afford 2-(2-phenethylamino)-2',3'-O-isopropylidene-adenosine-5'-(N-ethyl)-carboxamide.

EXAMPLE 2

Prepared in a similar manner are:
(a) 2-(2-phenethylamino)-adenosine-5'-(N-cyclopropyl)carboxamide, m.p. 115°–118°;
(b) 2-(p-methoxy-2-phenethylamino)-adenosine-5'-(N-ethyl)-carboxamide, m.p. 110°–115°;
(c) 2-(p-chloro-2-phenethylamino)-adenosine-5'-(N-elhyl)-carboxamide, m.p. 110°–115°;
(d) 2-(2-phenethylamino)-adenosine-5'-(N-methyl)carboxamide, m.p. 188°–190°;
(e) 2-(2-phenethylamino)-adenosine-5'-(N-2-hydroxyethyl)-carboxamide, m.p. 157°–160°;
(f) 2-(p-fluoro-2-phenethylamino)-adenosine-5'-(N-ethyl)-carboxamide, m.p. 108°–112°;
(g) 2-[p-(2-carboxyethyl)-2-phenethylamino]-adenosine5'-(N-ethyl)-carboxamide, m.p. 197°–202°; hydrochloride salt, m.p. 200°–203°; tromethamine salt, m.p. 100°; sodium salt, m.p. 160°–165°.

The amine starting material is prepared as follows:

A mixture of 5 g of p-bromophenylacetonitrile, 4.6 ml of t-butyl acrylate, 57 mg of palladium diacetate, 310 mg of tri-o-tolylphosphine and 12 ml of triethylamine is refluxed for 5 hours. The reaction mixture is diluted with ethyl acetate and washed with 10% HCl and saturated sodium bicarbonate solution. After drying over magnesium sulfate the solvent is removed in vacuo to yield t-butyl p-(cyanomethyl)-phenylacrylate. This material is dissolved in ethanol and hydrogenated over 1.1 g of 10% palladium on carbon catalyst for 3 days at 3 atmospheres pressure of hydrogen. After filtration the solvent is removed in vacuo and the residue is chromatagraphed on silica gel with ether/hexane (1:1) as the eluent to afford p-(2-t-butoxycarbonyl-ethyl)-phenyl-acetonitrile; 2.8 g of this material is dissolved in 90 ml of tetrahydrofuran and 50 ml of methanol and to this is added 6.2 g of cobalt chloride in 90 ml of water followed by 2.1 g of sodium borohydride in small portions. After filtration and removal of solvent, the residue is chromatagraphed on silica gel with 7.5% ammonia saturated methanol in methylene chloride as the eluent to afford p-(2-t-butoxy-carbonyl-ethyl)-2-phenethylamine as an oil.

(h) 2-p-(2-carboxyethenyl)-2-phenethylamino]-adenosine-5'-(N-ethyl)-carboxamide hydrochloride, m.p. 178°–181°.

The starting material is prepared by reduction of t-butyl p-(cyanomethyl)-phenylacrylate (as obtained in example 2 g) to p-t-butoxycarbonyl-ethenyl)-2-phenethylamine with sodium borohydride and cobalt chloride as described under g) above.

(i) 2-[p-(carboxymethoxy)-2-phenethylamino]-adenosine-5'-(N-ethyl)-carboxamide hydrochloride, m.p. 137°–141°;

The amine starting material is prepared as follows:

A mixture of 3 g of p-hydroxyphenylacetonitrile, 3.6 ml of t-butyl bromoacetate, 6.5 g of potassium carbonate in 45 ml of dimethylformamide is stirred at room temperature for 16 hours. After dilution with water the product is extracted with ether. The ethyl layer is washed with 1N sodium hydroxide, dried over magnesium sulfate and the solvent removed in vacuo to yield p-(t-butoxycarbonylmethoxy)-phenylacetonitrile which is reduced to p-(t-butoxycarbonylmethoxy)-2-phenethylamine with sodium borohydride/cobalt chloride as described for the starting material under (g).

(j) 2-(S-2-phenylpropylamino)-adenosine-5'-(N-ethyl)-carboxamide, m.p. 117-121°, prepared from the levorotatory (S)-2-phenylpropylamine, J. Med. Chem. 17, 717 (1974);

(k) 2-(N-methyl-2-phenethylamino)-adenosine-5'-(N-ethyl)-carboxamide, hydrochloride, m.p. 115°–119°, prepared from N-methylphenethylamine;

(l) 2-(p-carboxymethyl-2-phenethylamino)-adenosine-5'-(N-ethyl)-carboxamide hydrochloride, m.p. 140°–145°.

The amine starting material for compound (l) is prepared as follows:

A mixture of 20 g of p-bromophenylacetic acid, 30 ml of ether, 1 ml of sulfuric acid and 35 ml of isobutylene is shaken in a sealed bottle for 24 hours. The reaction mixture is diluted with ether and washed with sodium hydroxide solution. After drying over magnesium sulfate the ether is removed in vacuo to afford the t-butyl ester as an oil. A mixture of 9.6 g of this material is refluxed with a mixture of 6.1 g of N-vinylphthalimide, 160 mg of palladium acetate, 800 mg of tri-o-tolylphosphine, 10 ml of acetonitrile and 8 ml diisopropylethylamine for 24 hours. The reaction is diluted with water, the resulting precipitate is collected and recrystallized from methanol/methylene chloride. The resulting solid is hydrogenated at 4 atmospheres pressure over 2 g of 10% palladium on carbon catalyst in 100 ml of ethanol and 100 ml of tetrahydrofuran for 16 hours at room temperature. After removal of the solvent in vacuo the residue is heated at reflux with 10 ml of hydrazine hydrate and 20 ml of ethanol for 2 hours. The reaction is diluted with ether and washed with 5% potassium hydroxide solution. The ether is dried over magnesium sulfate solution and the solvent is removed in vacuo. The residue is chromatographed on silica gel, with 5% ammonia saturated methanol in methylene chloride as the eluent, to afford p-(t-butoxycarbonylmethyl)-2-phenethylamine as an oil.

(m) 2-[p-(dimethylaminocarbonylmethyl)-2-phenethylamino]-adenosine-5'-(N-ethyl)-carboxamide.

The amine starting material is prepared as follows:

A mixture of 6 g of p-bromophenylacetic acid in 100 ml of methylene chloride and 5 ml of oxalyl chloride is stirred at room temperature for 16 hours. After removal of the solvent in vacuo the residue is dissolved in methylene chloride and treated with excess dimethylamine at room temperature. After 1 hour the reaction mixture is washed with water, the organic layer is dried over magnesium sulfate and the solvent is removed in vacuo to afford p-bromo-N,N-dimethyl-phenylacetamide as an oil, which is converted to p-(dimethylaminocarbonylmethyl)-2-phenethylamine as described for the starting material under 1).

(n) 2-(2-cyclohexylethylamino)-adenosine-5'-(N-ethyl)-carboxamide hydrochloride, m.p. 154°–157°;
(o) 2-(2-cyclopentylethylamino)-adenosine-5'-(N-ethyl)-carboxamide;
(p) 2-(N-methyl-2-cyclohexylethylamino)-adenosine-5'-(N-ethyl)-carboxamide;
(q) 2-(p-carboxy-2-phenethylamino)-adenosine-5'-(N-ethyl)-carboxamide. The amine starting material is prepared using methodology under (1) from p-bromobenzoic acid.

EXAMPLE 3

The following compounds of formula Ia wherein $R_3'$ represents hydroxy can be prepared substantially according to the procedures previously described herein.

| Compound | NR'R$_1$' | R$_4$' |
|---|---|---|
| (a) | 3,4-dihydro-5-methoxy-2H-[1]-benzothiopyran-3-ylamino | CH$_2$CH$_3$ |
| (b) | 2-indanylamino | CH$_2$CH$_3$ |
| (c) | 1,2,3,4-tetrahydro-2-naphthylamino | CH$_2$CH$_3$ |
| (d) | 3,4-dihydro-2H-[1]-benzopyran-3-ylamino | CH$_2$CH$_3$ |
| (e) | NH—CH$_2$CH$_2$-p-C$_6$H$_4$—OCH$_2$CON(C$_2$H$_5$)$_2$ | CH$_2$CH$_3$ |
| (f) | 2,2-diphenylethylamino | CH$_2$CH$_3$ |
| (g) | 2-(2-pyridyl)-ethylamino | CH$_2$CH$_3$ |
| (h) | 2-(2-thienyl)-ethylamino | CH$_2$CH$_3$ |
| (i) | (9-9H-fluorenyl)-methylamino | CH$_2$CH$_3$ |
| (j) | N-methyl-2-(2-pyridyl)-ethylamino | CH$_2$CH$_3$ |
| (k) | N-methyl-2-(2-thienyl)-ethylamino | CH$_2$CH$_3$ |
| (l) | 2-(2-pyridyl)-propylamino | CH$_2$CH$_3$ |

The starting material for compound (a) is prepared as follows: To a cooled mixture of 30.6 g of m-methoxybenzenethiol, 54.4 g of 45% potassium hydroxide in 100 ml of dimethsulfoxide is added 36.0 g of alipha-(bromomethyl)acrylic acid in 25 ml of dimethylsulfoxide at such a rate as to maintain the reaction temperature at 50°–55°. After 1 hour the reaction mixture is diluted with water and washed with ether. After acidification, the product is extracted with ether, the organic layer is dried over magnesium sulfate and the solvent is removed in vacuo to afford alpha-(3-methoxybenzenethiomethyl)acrylic acid. This material is dissolved in 570 ml of o-dichlorobenzene and 7.2 g of triethylamine and heated to 200° for 5 hours. After cooling, the products are extracted with sodium bicarbonate solution, the aqueous layer is acidified and the products extracted with ether. After drying over magnesium sulfate, the solvent is removed in vacuo to afford a mixture of 3,4-dihydro-5-methoxy-2-H[1]-benzothiopyran-3-carboxylic acid and 3,4-dihydro-7-methoxy-2H-[1]-benzothiopyran-3-carboxylic acid.

This mixture of acids is dissolved in 500 ml of t-butyl alcohol and treated with 17 g of triethylamine and 36 ml of diphenylphosphoryl azide. After 5 hours reflux, the solvent is removed in vacuo and the residue is dissolved in ether and washed with 1N sodium hydroxide and 1N hydrochloric acid. After drying over magnesium sulfate, the solvent is removed in vacuo and the residue is chromatographed in silica gel (1 kg) with ether/hexane (1:4) as the eluent to afford in succession N-t-butoxycarbonyl-3,4-dihydro-5-methoxy-2H-[1]-benzothiopyran-3-amine and N-t-butoxycarbonyl-3,4-dihydro-7-methoxy-2H-[1]-benzothiopyran-3-amine.

A solution of 10 g of N-t-butoxycarbonyl-3,4-dihydro-5-methoxy-2H-[1]-benzothiopyran-3-amine in 30 ml of trifluoroacetic acid is kept at room temperature for 1 hour. The solvent is removed in vacuo, the residue is treated with 1N NaOH and the product is extracted with ether. After drying over magnesium sulfate, the solvent is removed in vacuo to afford 3,4-dihydro-5-methoxy-2H-[1]-benzothiopyran-3-amine as an oil.

EXAMPLE 4

A mixture of 2.70 g of 2-[p-(2-t-butoxycarbonylethyl)-2-phenethylamino]-2',3'-O-isopropylidene-adenosine-5'-(N-ethyl)-carboxamide and 45 ml of 1N hydrochloric acid is heated at 65° for 1 hour. The reaction mixture is cooled, the resulting precipitate is collected, washed first with ice water and then with a mixture of ethyl acetate and ether to yield 2-[p-(2-carboxyethyl)-2-phenethylamino]-adenosine-5'-(N-ethyl)-carboxamide hydrochloride, m.p. 200°–203° (of example 2 g);

The starting material is prepared as follows:
A mixture of 2.31 g of t-butyl p-(cyanomethyl)-phenylacrylate (example 2g), 6.28 g of concentrated aqueous ammonium hydroxide and 0.46 g of 5% rhodium on alumina in 50 ml of absolute ethanol is hydrogenated at 3 atmospheres pressure and room temperature for 22 hours. A second portion of 0.46 g of rhodium on alumina is added and hydrogenation is continued for 6 more hours. The reaction mixture is filtered, the catalyst is washed with ethanol, and the filtrate is evaporated to dryness. The residue is dissolved in 50 ml of ethyl acetate, hydrogen chloride gas is bubbled into the solution for 10 minutes and the solution is evaporated to dryness. The product is triturated with ether and collected to yield p-(2-t- butoxycarbonylethyl)-2-phenethylamine hydrochloride which is then converted to the free base.

A mixture of 4.0 g of 2-chloro-2',3'-O-isopropylidene-adenosine-5'-(N-ethyl)-carboxamide and 14.0 g of p-(2-t-butoxycarbonylethyl)-2-phenethylamine is heated at 130° for 3 hours. The reaction mixture is dissolved in methylene chloride, the solution is washed with sodium bicarbonate solution and evaporated to dryness. The residue is crystallized from ether to yield 2-[p-(2-t-butoxycarbonylethyl)-2-phenethylamino]-2',3'-O-isopropylidene-adenosine-5'-(N-ethyl)-carboxamide, m.p. 180°.

EXAMPLE 5

A solution of 12 mg of 2$\beta$-{2-[p-(2-t-butoxycarbonylethyl)-2-phenethylamino]-9-adenyl}-3-alpha-hydroxy-2,3-dihydrofuran-5-N-ethylcarboxamide in 1.5 ml of ethanol to which is added 10 mg of 5% rhodium on carbon is hydrogenated at room temperature and 3 atmospheres pressure for 30 hours. The catalyst is filtered off and the solution is evaporated to dryness to yield a mixture of isomers comprising 2-[p-(2-carboxyethyl)-2-phenethylamino]-3'-deoxyadenosine-5'-(N-ethyl)-carboxamide; NMR (CD$_3$OD): 8.0 (s,1H), 5.93 (d,1H).

The starting material is prepared as follows:
Sodium hydride (6 mg of 60% dispersion in mineral oil) is added to a solution of 20 mg of 2-[p-(2-t-butoxycarbonylethyl)-2-phenethylamino]-2',3'-O-isopropylidene-adenosine-5'-(N-ethyl)-carboxamide in 25 ml of anhydrous isopropanol. The reaction mixture is heated at 70° for 6 hours. The reaction mixture is cooled and the reaction is quenched with 0.5 ml pH6 phosphate buffer, and the mixture is evaporated to dryness. The resulting product is chromatographed on silica gel eluting with 10% methanol in methylene chloride to yield 2-{2β-[p-(2-t-butoxycarbonyl-ethyl)-2-phenethylamino]-9-adenyl}-3-alpha-hydroxy-2,3-dihydrofuran-5-N-ethylcarboxamide as an oil; NMR (CD$_3$OD): 7.82 (s,1H), 6.36 (d,1H), 6.1 (d,1H), 5.52 (t,1H).

EXAMPLE 6

(a) A mixture of 1.05 g of 2-[p-(2-carboxyethyl)-2phenethylamino]-adenosine-5'-(N-ethyl)-carboxamide sodium salt and 314 mg of ethyl iodide in 10 ml of dimethylformamide is stirred at room temperature for 16 hours. The reaction mixture is poured onto water and the product is extracted with ethyl acetate. After drying over magnesium sulfate the solvent is removed in vacuo and the residue is triturated with ether to afford 2-[p-(2)carboxyethyl)-2-phenethylamino]-adenosine-5'-(N-ethyl)-carboxamide ethyl ester m.p. 81°–89°, the compound of formula IIa wherein $R_4$ represents ethyl, $R_5$, $R_6$, $R_7$ and $R_8$ represent hydrogen, and $R_9$ represents p-(2-ethoxycarbonylethyl)-phenyl.

Prepared in a similar fashion are the following:
(b)  2-[p-(2-carboxyethyl)-2-phenethylamino]-adenosine5'-(N-ethyl)-carboxamide pivaloyloxymethyl ester, m.p. 85°–89°;
(c)  2-[p-(2-carboxyethyl)-2-phenethylamino]-adenosine5'-(N-ethyl)-carboxamide methyl ester, m.p. 90°–95°;
(d)  2-[p-(2-carboxyethyl)-2-phenethylamino]-adenosine5'-(N-ethyl)-carboxamide 2-N,N-dimethylaminoethyl ester;
(e) 2-[p-(2-carboxyethyl)-2-phenethylamino]-adenosine-5'-(N-ethyl)-carboxamide n-butyl ester, m.p. 68°–75°.

EXAMPLE 7

The following compounds can be prepared substantially according to the procedures described herein.
(a) 2-(3-cyclohexylpropylamino)-adenosine-5'-(N-ethyl)-carboxamide hydrochloride, m.p. 175°–181°;
(b) 2-(4-cyclohexylbutylamino)-adenosine-5'-(N-ethyl)-carboxamide hydrochloride, m.p. 130°–134°;
(c) 2-[2-(2-norbornanyl)-ethylamino]-adenosine-5'-N-ethylcarboxamide;
(d) 2-[2-(1-adamantyl)-ethylamino]-adenosine-5'-N-ethylcarboxamide;
(e) 2-[2-(1-cyclohexenyl)-ethylamino]-adenosine-5'-N-ethylcarboxamide;
(f) 2-[2-(tetrahydropyran-4-yl)-ethylamino]-adenosine-5'-N-ethylcarboxamide; the starting 2-(tetrahydropyran-4-yl)-ethylamine can be prepared from tetrahydropyran-4-one e.g. by Wittig condensation with diethyl cyanomethyl phosphonate followed by hydrogenation and reduction with lithium aluminum hydride.
(g) 2-(p-hydroxy-2-phenethylamino)-adenosine-5'-(N-ethyl)-carboxamide, m.p. 110°–116°.
(h) 2-(3-phenylpropylamino)-adenosine-5'-(N-ethyl)carboxamide, hydrochloride salt, m.p. 114°–120°.
(i) 2-(4-phenylbutylamino)-adenosine-5'-(N-ethyl)carboxamide, hydrochloride salt, m.p. 115°–120°.
(j) 2-[p-carboxyethyl)-2-phenethylamino]-adenosine-5'-(N-ethyl)-carboxamide benzyl ester, m.p. 75°–80°.
(k) 2-(β-hydroxy-β-methyl-2-phenethylamino)-adenosine-5'-(N-ethyl)-carboxamide, m.p. 124°–130°, alpha]D = +4.94° (EtOH), prepared from R(-)-β-hydroxy-β-methyl-2-phenethylamine.
(l) 2-(β-hydroxy-β-methyl-2-phenethylamino)-adenosine-5'-(N-ethyl)-carboxamide, m.p. 115°–120°, alpha]$_D$ = +29.06° (EtOH), prepared from S(+)-β-hydroxy-β-methyl-2-phenethylamine.

EXAMPLE 8

A solution of 2-(p-hydroxy-2-phenethylamino)-adenosine-5'-(N-ethyl)-carboxamide (170 mg) in dimethylformamide (1 mL) is treated with 0.3 M aqueous disodium hydrogen phosphate (0.65 mL) followed by chloramine T hydrate (17.8 mg) and sodium iodide (117 mg). After 3 hours of stirring, chloramine-T hydrate (17.8 mg) and sodium iodide (117 mg) are again added and the whole stirred overnight. More chloramine-T (17.8 mg) is added and after a further 3 hour period, the solvent is removed under high vacuum and the residue treated with excess aqueous sodium thiosulfate and extracted with ethyl acetate. The organic extract is washed with brine, dried over sodium sulphate and chromatographed over silica gel with 10% methanol in methylene chloride as eluent. The desired fractions are combined and concentrated to dryness at reduced pressure to afford 2-[(4-hydroxy-3-iodo)2-phenethylamino]-adenosine-5'-(N-ethyl)-carboxamide, m.p. 131°–140°.

EXAMPLE 9

A mixture of 2-[p-(2-carboxyethyl)-2-phenethylamino]-adenosine-5'-(N-ethyl)-carboxamide benzyl ester (0.4 g), pyridine (10 mL) and acetic anhydride (1 mL) is stirred at room temperature under nitrogen for 2 hours. The mixture is concentrated under high vacuum, taken up in ethyl acetate, washed with cold dilute sodium bicarbonate solution, washed with brine, dried over sodium sulfate and concentrated to dryness to afford 2-[p-(2-carboxyethyl)-2-phenethylamino]-2'3'-di-O-acetyl-adenosine-5'-(N-ethyl)-carboxamide benzyl ester as an oil.

EXAMPLE 10

A solution of 2-[p-(2-carboxyethyl)-2-phenethylamino]-2'3'-di-O-acetyl-adenosine-5'-(N-ethyl)-carboxamide benzyl ester (0.45 g) in ethanol (100 mL) is hydrogenated at 50 p.s.i. at room temperature over 5 hours in the presence of 10% Pd on carbon (0.5 g). The mixture is filtered and the filtrate concentrated to dryness to afford 2-[p-(2-carboxyethyl)-2-phenethylamino]-2',3'-di-O-acetyl-adenosine-5'-(N-ethyl)-carboxamide, m.p. 113°–117°, [alpha]$_D$ = +5.0° (c=1.28, MeOH).

EXAMPLE 11

Prepared similarly to procedures described in examples 9 and 10 are:
(a) 2-[p-(2-carboxyethyl)-2-phenethylamino]-2',3-di-O-n-propionyl-adenosine-5'-(N-ethyl)-carboxamide;
(b) 2-carboxyethyl)-2-phenethylamino]-2',3'-di-O-butyryl-adenosine-5'-(N-ethyl)-carboxamide;
(c) 2-[p-(2-carboxyethyl)-2-phenethylamino]-2,3'-di-O-benzoyl-adenosine-5'-(N-ethyl)-carboxamide;
(d) 2-[p-(2-carboxyethyl)-2-phenethylamino]-2,3'-di-O-nicotinoyl-adenosine-5'-(N-ethyl)-carboxamide.

EXAMPLE 12

A mixture of 500 mg of 2-[p-(2-carboxyethyl)-2-phenethylamino]-adenosine-5'-(N-ethyl)-carboxamide, 205 mg of 1,3-dicyclohexylcarbodiimide and 122 mg of phenethylamine in 15 ml of methylene chloride is stirred overnight at room temperature. The reaction is poured into 50 ml of methylene chloride and washed with 25 ml of 10% aqueous sodium bicarbonate and 25 ml of water. The organic layer is dried over magnesium sulfate and evaporated to give a crude product which is purified by flash column chromatography using 9:1 methylene chloride-methanol saturated with ammonia to give 2-[p-(2-phenethylaminocarbonylethyl)-2-phenethylamino]-adenosine-5'-(N-ethyl)-carboxamide.

EXAMPLE 13

The following compounds of formula I wherein R and $R_2$ represent hydrogen, $R_3$ represents hydroxy and $R_4$ represents ethyl can be prepared substantially according to procedures described above.

| COMPOUND | $R_1$ |
|---|---|
| (a) | p-[2-(3-indolylethylaminocarbonyl)ethyl]-2-phenethyl |
| (b) | p-[2-(3-morpholinopropylaminocarbonyl)ethyl]-2-phenethyl |
| (c) | p-[2-(4-hydroxyphenethylaminocarbonyl)ethyl]-2-phenethyl |
| (d) | p-[2-(decylaminocarbonyl)ethyl]-2-phenethyl |
| (e) | p-{2-[5-(ethoxycarbonylpentyl)aminocarbonyl]-ethyl}-2-phenethyl |
| (f) | p-{2-[3-(N-pyrrolidin-2-onyl)propylaminocarbonyl]-ethyl}-2-phenethyl |
| (g) | p-[2-(4-benzylpiperidinocarbonyl)ethyl]-2-phenethyl |
| (h) | p-[2-(4-benzylpiperazinocarbonyl)ethyl]-2-phenethyl |
| (i) | p-[2-(3-dimethylaminopropylaminocarbonyl)ethyl]-2-phenethyl |
| (j) | p-[2-(4-ethoxycarbonylpiperidinocarbonyl)]-2-phenethyl |
| (k) | p-[2-(4-ethoxycarbonylpiperazinocarbonyl)ethyl]-2-phenethyl |
| (l) | p-{2-[4-(2-pyridyl)-piperazinocarbonyl]ethyl}-2-phenethyl |

EXAMPLE 14

(a) Preparation of 10,000 tablets each containing 10 mg of the active ingredient:
Formula:

| | |
|---|---|
| 2-(2-phenethylamino)-adenosine-5'-(N-ethyl)-carboxamide | 100.00 g |
| Lactose | 2,400.00 g |
| Corn starch | 125.00 g |
| Polyethylene glycol 6,000 | 150.00 g |
| Magnesium stearate | 40.00 g |
| Purified water | q.s |

Procedure:
All the powders are passed through a screen with openings of 0.6 mm. Then the drug substance, lactose, magnesium stearate and half of the starch are mixed in a suitable mixer. The other half of the starch is suspended in 65 ml of water and the suspension added to the boiling solution of the polyethylene glycol in 260 ml of water. The paste formed is added to the powders, which are granulated, if necessary, with an additional amount of water. The granulate is dried overnight at 35°, broken on a screen with 1.2 mm openings and compressed into tablets, using concave punches uppers bisected.

(b) Preparation of 1,000 capsules each containing 10 mg of the active ingredient: Formula:

| | |
|---|---|
| 2-[p-(2-carboxyethyl)-2-phenethylamino] adenosine-5'-(N-ethyl)-carboxamide hydrochloride | 10.0 g |
| Lactose | 207.0 g |
| Modified starch | 80.0 g |
| Magnesium stearate | 3.0 g |

Procedure:
All the powders are passed through a screen with openings of 0.6mm. Then the drug substance is placed in a suitable mixer and mixed first with the magnesium stearate, then with the lactose and starch until homogeneous. No. 2 hard gelatin capsules are filled with 300 mg of said mixture each, using a capsule filling machine.

(c) Similarly prepared are capsules and tablets comprising other compounds exemplified herein, e.g. 2-(2-cyclohexylethyl)-adenosine-5'-(N-ethyl)-carboxamide, 2-[p-(2-carboxyethyl)-2-phenethylamino]-adenosine-5'-(N-ethyl)-carboxamide ethyl ester.

What is claimed is:

1. A compound according to claim 1 of formula II

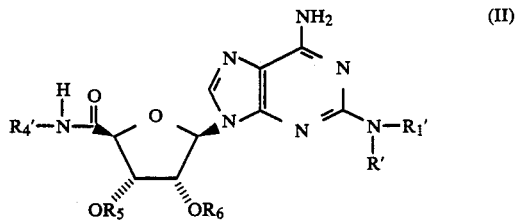

wherein R' represents hydrogen or $C_1$–$C_4$-alkyl; $R_1'$ represents ($C_5$- or C6)-cycloalkyl-$C_1$–$C_4$-alkyl, or $R_1'$ represents aryl-$C_1$–$C_4$-alkyl in which aryl represents 2- or 3-thienyl, 2-, 3- or 4-pyridyl, phenyl, or phenyl monosubstituted by halogen, trifluoromethyl, lower alkoxy, lower alkyl or by a substituent -W-Z in which W represents a direct bond, $C_1$–$C_4$-alkylene, thio-$C_1$–$C_3$-alkylene or oxy-$C_1$–$C_3$-alkylene and Z represents cyano, carboxy, lower alkoxycarbonyl, carbamoyl, N-mono- or N,N-di-lower alkylcarbamoyl; or $R_1'$ represents aryl-hydroxy-$C_1$–$C_4$-alkyl in which aryl has meaning as defined above; $R_4'$ represents $C_1$–$C_4$-alkyl, cyclopropyl or hydroxy-$C_2$–$C_4$-alkyl; $R_5$ and $R_6$ represent hydrogen, lower alkanoyl, lower alkoxy-lower alkanoyl, aroyl, carbamoyl, or mono- or di-lower alkylcarbamoyl; or a pharmaceutically acceptable salt thereof.

2. A compound according to claim 1 of formula II wherein R' represents $C_1$–$C_3$-alkyl or hydrogen; $R_1'$ represents $CH_2CH_2$-(cyclohexyl or cyclopentyl); or $R_1'$ represents —$CH_2CH_2$-aryl in which aryl represents 2- or 3 represents pyridyl, phenyl, or phenyl monosubstituted by a substituent -$CH_2CH_2$-Z or -$OCH_2$-Z in which Z represents cyano, carboxy, lower alkoxycarbonyl, carbamoyl, N-mono- or N,N-di-lower alkylcarbamoyl; $R_4'$ represents ethyl or hydroxyethyl; $R_5$ and $R_6$ represent hydrogen, lower alkanoyl or lower alkoxy-$C_2$–$C_4$-alkanoyl; or a pharmaceutically acceptable salt thereof.

3. A compound according to claim 1 of formula II wherein R' represents hydrogen or methyl; $R_1'$ represents cyclohexylethyl; or $R_1'$ represents 2-phenylethyl, 2-(2-pyridyl)-ethyl or 2-phenylethyl substituted in the para position by $CH_2CH_2Z$ in which Z represents carboxy, lower alkoxycarbonyl, carbamoyl or mono-lower alkylcarbamoyl; $R_4'$ represents ethyl; $R_5$ and $R_6$ represent hydrogen; or a pharmaceutically acceptable salt thereof.

4. A compound according to claim 6 of formula IIa

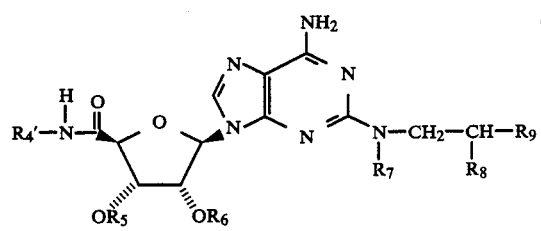

wherein $R_4'$ represents ethyl; $R_5$ and $R_6$ represent hydrogen or lower alkanoyl; $R_7$ represents hydrogen or methyl; $R_8$ represents hydrogen or methyl; $R_9$ represents cyclohexyl, phenyl or phenyl monosubstituted by halogen, trifluoromethyl, lower alkyl, lower alkoxy or -CH$_2$CH$_2$-Z in which Z represents carboxy or lower alkoxycarbonyl; or pharmaceutically acceptable salt thereof.

5. A compound according to claim 4 wherein $R_7$ represents hydrogen.

6. A compound according to claim 4 being 2-(2-phenethylamino)-adenosine-5'-(N-ethyl)-carboxamide or a pharmceutically acceptable salt thereof.

7. A compound according to claim 4 being 2-[p-(2-carboxyethyl)-2-phenethylamino]-adenosine-5'-(N-ethyl)carboxamide or a pharmaceutically acceptable salt thereof.

8. A compound according to claim 4 being 2-[p-(carboxymethoxy)-2-phenethylamino]-adenosine-5'-(N-ethyl)carboxamide or a pharmaceutically acceptable salt thereof.

9. A compound according to claim 4 being 2-(p-methoxy-2-phenethylamino)-adenosine-5'-(N-ethyl)-carboxamide or a pharmaceutically acceptable salt thereof.

10. A compound according to claim 4 being 2-(p-chloro-2-phenethylamino)-adenosine-5'-(N-ethyl)-carboxamide or a pharmaceutically acceptable salt thereof.

11. A compound according to claim 4 being 2-(2-cyclohexylethylamino)-adenosine-5'-(N-ethyl)-carboxamide or a pharmaceutically acceptable salt thereof.

12. A compound according to claim 4 being 2-[p-(2-carboxyethyl)-2-phenethylamino]-2',3'-di-O-acetyl-adenosine-5'-(N-ethyl)-carboxamide or a pharmaceutically acceptable salt thereof.

13. A compound according to claim 4 being 2-[p-(2-carboxyethyl)-2-phenethylamino]-adenosine-5'-(N-ethyl)-carboxamide ethyl ester or a pharmaceutically acceptable salt thereof.

14. A antihypertensive pharmaceutical composition suitable for administration to a mammal in need thereof comprising an effective amount of a compound of claim 1 in combination with one or more pharmaceutically acceptable carriers.

15. A method of treating hypertension in mammals comprising the administration to a mammal in need thereof of an effective antihypertensive amount of a compound of claim 1 or of a pharmaceutical composition comprising a said compound.

* * * * *